US011363939B2

(12) United States Patent
Ariyoshi et al.

(10) Patent No.: US 11,363,939 B2
(45) Date of Patent: Jun. 21, 2022

(54) ENDOSCOPE SYSTEM, OPERATION METHOD OF ENDOSCOPE SYSTEM AND RECORDING MEDIUM

(71) Applicant: OLYMPUS CORPORATION, Tokyo (JP)

(72) Inventors: Daiki Ariyoshi, Chofu (JP); Risa Arai, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 21 days.

(21) Appl. No.: 17/123,626

(22) Filed: Dec. 16, 2020

(65) Prior Publication Data

US 2021/0100426 A1 Apr. 8, 2021

Related U.S. Application Data

(63) Continuation of application No. PCT/JP2019/007351, filed on Feb. 26, 2019.

(30) Foreign Application Priority Data

Jun. 19, 2018 (JP) .............................. JP2018-116044

(51) Int. Cl.
*A61B 1/00* (2006.01)
*G06T 7/90* (2017.01)
(Continued)

(52) U.S. Cl.
CPC ........ *A61B 1/00006* (2013.01); *A61B 1/0005* (2013.01); *A61B 1/05* (2013.01);
(Continued)

(58) Field of Classification Search
None
See application file for complete search history.

(56) References Cited

U.S. PATENT DOCUMENTS

2002/0014595 A1* 2/2002 Sendai ................. A61B 1/0005
250/458.1
2002/0016620 A1* 2/2002 Tsujita ............... A61B 1/00006
607/88
(Continued)

FOREIGN PATENT DOCUMENTS

EP 1177761 A2 2/2002
EP 1609407 A1 12/2005
(Continued)

OTHER PUBLICATIONS

International Search Report dated May 28, 2019 issued in PCT/JP2019/007351.

*Primary Examiner* — Rebecca A Volentine
(74) *Attorney, Agent, or Firm* — Scully, Scott, Murphy & Presser, P.C.

(57) ABSTRACT

An endoscope system includes a light source configured to generate either one of first illumination light and second illumination light, an image pickup apparatus configured to obtain an image by picking up an image of an object, and a processor. The processor is configured to make an instruction to set an observation mode of the endoscope system at either one of a first observation mode and a second observation mode, detect an observation state at a time of observing the object based on a feature value calculated from pixel values included in pixels forming a first image, and invalidate an instruction to set the observation mode of the endoscope system at the second observation mode when the observation state at the time of observing the object is not an appropriate observation state.

15 Claims, 5 Drawing Sheets

(51) Int. Cl.
*A61B 1/05* (2006.01)
*A61B 1/06* (2006.01)
*G06T 7/00* (2017.01)

(52) U.S. Cl.
CPC .......... *A61B 1/0638* (2013.01); *G06T 7/0012* (2013.01); *G06T 7/90* (2017.01); *G06T 2207/10024* (2013.01); *G06T 2207/10068* (2013.01); *G06T 2207/10152* (2013.01)

(56) References Cited

U.S. PATENT DOCUMENTS

2007/0191677 A1* 8/2007 Nishimura ......... A61B 1/00016
600/109
2009/0259098 A1 10/2009 Krattiger

FOREIGN PATENT DOCUMENTS

| EP | 1609408 A1 | 12/2005 |
| EP | 1609409 A1 | 12/2005 |
| JP | 2002-45330 A | 2/2002 |
| JP | 2010-99171 A | 5/2010 |
| JP | 1632645 B2 | 2/2011 |
| JP | 2012-50641 A | 3/2012 |
| WO | 2018/083879 A1 | 5/2018 |

* cited by examiner

ENDOSCOPE SYSTEM, OPERATION METHOD OF ENDOSCOPE SYSTEM AND RECORDING MEDIUM

CROSS REFERENCE TO RELATED APPLICATION

This application is a continuation application of PCT/JP2019/007351 filed on Feb. 26, 2019 and claims benefit of Japanese Application No. 2018-116044 filed in Japan on Jun. 19, 2018, the entire contents of which are incorporated herein by this reference.

BACKGROUND OF THE INVENTION

1. Field of the Invention

The present invention relates to an endoscope system, an operation method of the endoscope system, and a recording medium, and particularly relates to an endoscope system used for observation of living tissue, an operation method of the endoscope system, and a recording medium.

2. Description of the Related Art

In endoscope observation in the medical field, as the art that assists diagnosis of an abnormal site existing in a subject, there has been conventionally known an art that generates and displays a diagnosis assist image having a color and/or a pattern allowing for identifying the abnormal site included in an endoscope image by applying processing to the endoscope image obtained by picking up an image of the object including living tissue existing in the subject, for example.

More specifically, for example, Japanese Patent No. 4632645 discloses the art that calculates a scattering feature by living tissue by applying processing to image data obtained by picking up an image of the living tissue in a body cavity by an electronic endoscope, and generates and displays a color image having a display color corresponding to the calculated scattering feature.

Here, the color and/or the pattern included in the aforementioned diagnosis assist image can change in response to the observation direction and the observation state such as brightness at the time of observing the object in the subject, for example.

SUMMARY OF THE INVENTION

An endoscope system of one aspect of the present invention includes a light source configured to generate either one of first illumination light and second illumination light as illumination light for illuminating an object, an image pickup apparatus configured to obtain an image by picking up an image of the object illuminated by the illumination light, and a processor, wherein the processor is configured to make an instruction to set an observation mode of the endoscope system at either one of a first observation mode in which a display apparatus is caused to display a first image obtained by picking up an image of the object illuminated by the first illumination light, and a second observation mode in which the display apparatus is caused to display a third image obtained by processing at least one of a color and a pattern of a second image obtained by picking up an image of the object illuminated by the second illumination light, detect an observation state at a time of observing the object by an endoscope provided with the image pickup apparatus, based on a feature value calculated from pixel values included in pixels forming the first image, and invalidate an instruction to set the observation mode of the endoscope system at the second observation mode, when the processor detects that the observation state at the time of observing the object by the endoscope is not an appropriate observation state based on a result of the detection, immediately before the observation mode of the endoscope system is switched from the first observation mode to the second observation mode.

An operation method of an endoscope system of one aspect of the present invention includes generating, by a light source, either one of first illumination light and second illumination light as illumination light for illuminating an object, acquiring, by an image pickup apparatus, an image by picking up an image of the object illuminated by the illumination light, and making, by a processor, an instruction to set an observation mode of the endoscope system at either one of a first observation mode in which a display apparatus is caused to display a first image obtained by picking up an image of the object illuminated by the first illumination light, and a second observation mode in which the display apparatus is caused to display a third image obtained by processing at least one of a color and a pattern of a second image obtained by picking up an image of the object illuminated by the second illumination light, detecting, by the processor, an observation state at a time of observing the object by an endoscope provided with the image pickup apparatus based on a feature value calculated from pixel values included in pixels forming the first image, and invalidating, by the processor, an instruction to set the observation mode of the endoscope system at the second observation mode, when detecting that the observation state at the time of observing the object by the endoscope is not an appropriate observation state based on a result of the detection, immediately before the observation mode of the endoscope system is switched from the first observation mode to the second observation mode.

A computer-readable non-transitory recording medium of one aspect of the present invention causes an endoscope system to execute processing of generating either one of first illumination light and second illumination light as illumination light for illuminating an object, processing of acquiring an image by picking up an image of the object illuminated by the illumination light, processing of making an instruction to set an observation mode of the endoscope system at either one of a first observation mode in which a display apparatus is caused to display a first image obtained by picking up an image of the object illuminated by the first illumination light, and a second observation mode in which the display apparatus is caused to display a third image obtained by processing at least one of a color and a pattern of a second image obtained by picking up an image of the object illuminated by the second illumination light, processing of detecting an observation state at a time of observing the object by an endoscope provided with an image pickup apparatus based on a feature value calculated from pixel values included in pixels forming the first image, and processing of invalidating an instruction to set the observation mode of the endoscope system at the second observation mode, when detecting that the observation state at the time of observing the object by the endoscope is not an appropriate observation state based on a result of the detection, immediately before the observation mode of the endoscope system is switched from the first observation mode to the second observation mode.

DETAILED DESCRIPTION OF THE PREFERRED EMBODIMENT(S)

Hereinafter, an embodiment of the present invention will be described with reference to the drawings.

FIG. 1 to FIG. 9 relate to the embodiment of the present invention.

Figure 1:
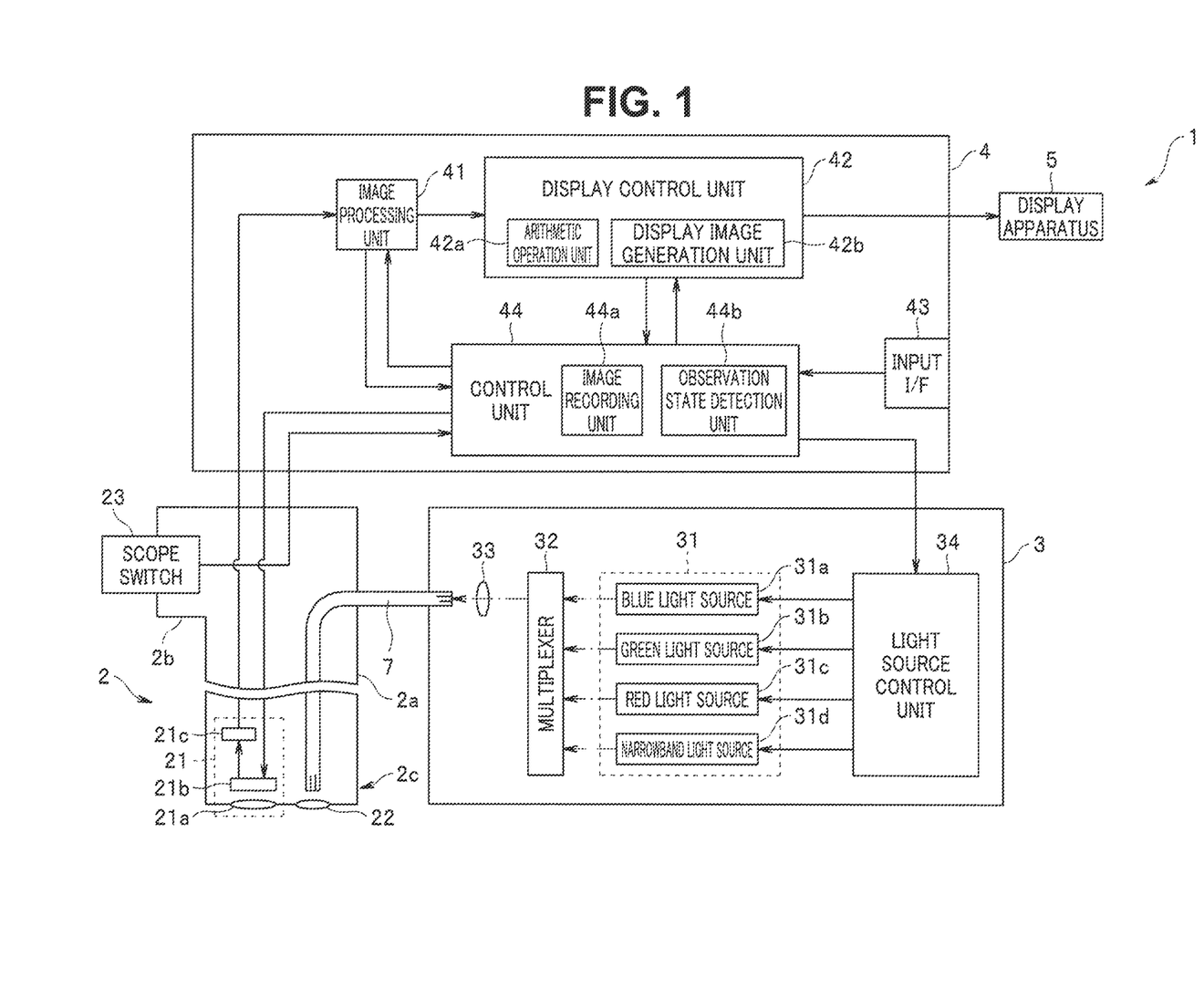
FIG. 1 is a diagram illustrating a configuration of an essential part of an endoscope system according to an embodiment.

As illustrated in FIG. 1, an endoscope system 1 has an endoscope 2, a light source apparatus 3, a processor 4, and a display apparatus 5. The endoscope 2 is insertable into a subject, and is configured to pick up an image of an object such as living tissue existing in the subject and output an obtained endoscope image. The light source apparatus 3 is configured to supply illumination light used for observation of the object via a light guide 7 that is inserted through and disposed in an inside of the endoscope 2. The processor 4 is configured to perform an operation to output a display image corresponding to the endoscope image outputted from the endoscope 2. The display apparatus 5 is configured to display the display image and the like outputted from the processor 4 onto a screen. FIG. 1 is a diagram illustrating a configuration of an essential part of the endoscope system according to the embodiment.

The endoscope 2 has an insertion portion 2a that is insertable into a subject and is formed into an elongated shape, and an operation portion 2b provided at a proximal end side of the insertion portion 2a. The endoscope 2 is configured to be attachably and detachably connected to the processor 4 via a universal cable (not illustrated) containing a signal line used for transmission of an endoscope image and the like outputted from an image pickup unit 21 (described later), for example. The endoscope 2 is configured to be attachably and detachably connected to the light source apparatus 3 via a light guide cable (not illustrated) containing at least a part of the light guide 7.

In a distal end portion 2c of the insertion portion 2a, the image pickup unit 21, an emission end portion of the light guide 7, and an illumination optical system 22 are provided. The image pickup unit 21 is to pick up an image of an object such as living tissue in a subject. The illumination optical system 22 is configured to irradiate the object with the illumination light transmitted by the light guide 7.

The image pickup unit 21 is configured to pick up an image of the object illuminated by the illumination light that passes through the illumination optical system 22 to generate an endoscope image, and output the generated endoscope image to the processor 4. In other words, the image pickup unit 21 is configured to pick up the image of the object illuminated with the illumination light passing through the illumination optical system 22 to obtain the endoscope image. The image pickup unit 21 is configured by having an objective optical system 21a, an image pickup device 21b, and an analog front end (hereinafter, abbreviated as APE) 21c.

The objective optical system 21a has, for example, an optical element such as a lens, and is configured to form an image of return light (reflected light) emitted from an object illuminated with the illumination light passing through the illumination optical system 22.

The image pickup device 21b is configure by including an image sensor such as a CCD or a CMOS. On an image pickup surface of the image pickup device 21b, a color filter with a primary color Bayer array, and a plurality of pixels are provided. The color filter with a primary color Bayer array is configured to split the return light incident from the objective optical system 21a into three colors that are red, green and blue. The plurality of pixels are arranged in a matrix shape to pick up an image of the light passing through the color filter. The image pickup device 21b is configured to generate an image pickup signal by picking up an image of the return light the image of which is formed by the objective optical system 21a, and output the generated image pickup signal to the AFE 21c. The image pickup device 21b is configured to perform an operation corresponding to a control signal outputted from the processor 4.

The AFE 21c is configured to generate an endoscope image (endoscope image data) by applying predetermined signal processing such as noise reduction processing, and A/D conversion processing to the image pickup signal outputted from the image pickup device 21b, and output the generated endoscope image to the processor 4.

The operation portion 2b is configured by including such a shape that a user can grasp and operate the operation portion 2b. The operation portion 2b is provided with a scope switch 23 configured by including one or more switches capable of making an instruction corresponding to an input operation of the user to the processor 4. More specifically, the scope switch 23 is provided with an observation mode changeover switch (not illustrated) capable of making an instruction to set (switch) an observation mode of the endoscope system 1 at either a normal observation mode or a diagnosis assist mode in response to the operation of the user, for example. Further, the scope switch 23 is provided with a release switch (not illustrated) capable of making a release instruction to cause an endoscope image that is obtained by picking up an image of an object by the endoscope 2 to be recorded as a still image in response to an operation of the user, for example.

In other words, the scope switch 23 includes a function as a switching instruction unit, and is configured to be able to make an instruction to set the observation mode (of the endoscope system 1) at a time of observing an object an image of which is picked up by the endoscope 2 at either one of the normal observation mode, and the diagnosis assist mode. The normal observation mode is to cause the display apparatus 5 to display an endoscope image WDI (described later). The diagnosis assist mode is to cause the display apparatus 5 to display a diagnosis assist image SDS (describe later) in which at least one of a color and a pattern of an endoscope image SDI (described later) is processed.

The light source apparatus 3 has a function as a light source unit, and is configured to generate either one of illumination light WL and illumination light SL (both will be described later) as the illumination light for illuminating an object existing in a subject. The light source apparatus 3 is configured by having a light emitting unit 31, a multiplexer 32, a condensing lens 33, and a light source control unit 34.

The light emitting unit 31 is configured by having a blue light source 31*a*, a green light source 31*b*, a red light source 31*c*, and a narrowband light source 31*d*.

Figure 2:
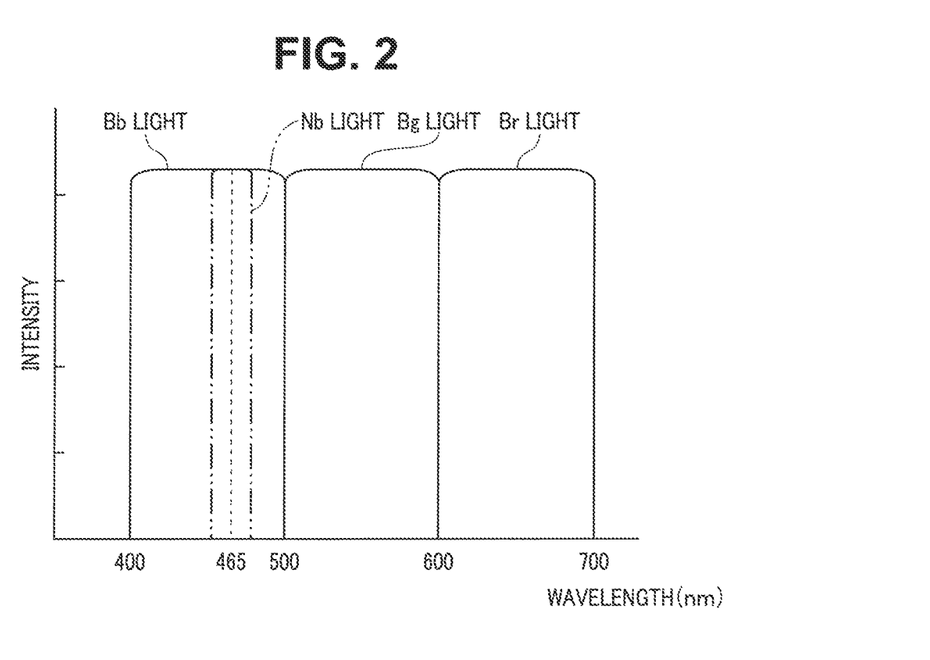
FIG. 2 is a diagram illustrating one example of wavelength bands of light emitted from a light source apparatus of the endoscope system according to the embodiment.

The blue light source 31*a* is configured by having a light emitting element such as a blue LED, for example. The blue light source 31*a* is configured to generate blue light (hereinafter, referred to as a Bb light) having intensity in a blue region. More specifically, the blue light source 31*a* is configured to generate light having intensity in a wavelength band of 400 nm to 500 nm as the Bb light, as illustrated in FIG. 2, for example. The blue light source 31*a* is configured to emit light or quench light in response to a light source driving signal that is supplied from the light source control unit 34. The blue light source 31*a* is configured to emit light with an emission light amount corresponding to a light source driving signal supplied from the light source control unit 34. FIG. 2 is a diagram illustrating one example of wavelength bands of the light emitted from the light source apparatus of the endoscope system according to the embodiment.

The green light source 31*b* is configured by having a light emitting element such as a green LED, for example. The green light source 31*b* is configured to generate green light (hereinafter, referred to as a Bg light) having intensity in a green region. More specifically, the green light source 31*b* is configured to generate light having intensity in a wavelength band of 500 nm to 600 nm as the Bg light, as illustrated in FIG. 2, for example. The green light source 31*b* is configured to emit light or quench light in response to a light source driving signal that is supplied from the light source control unit 34. The green light source 31*b* is configured to emit light with an emission light amount corresponding to a light source driving signal supplied from the light source control unit 34.

The red light source 31*c* is configured by having a light emitting element such as a red LED, for example. The red light source 31*c* is configured to generate red light (hereinafter, referred to as a Br light) having intensity in a red region. More specifically, the red light source 31*c* is configured to generate light having intensity in a wavelength band of 600 nm to 700 nm as the Br light, as illustrated in FIG. 2, for example. The red light source 31*c* is configured to emit light or quench light in response to a light source driving signal that is supplied from the light source control unit 34. The red light source 31*c* is configured to emit light with an emission light amount corresponding to a light source driving signal supplied from the light source control unit 34.

The narrowband light source 31*d* is configured by having a light emitting element such as a blue LED, for example.

Figure 3:
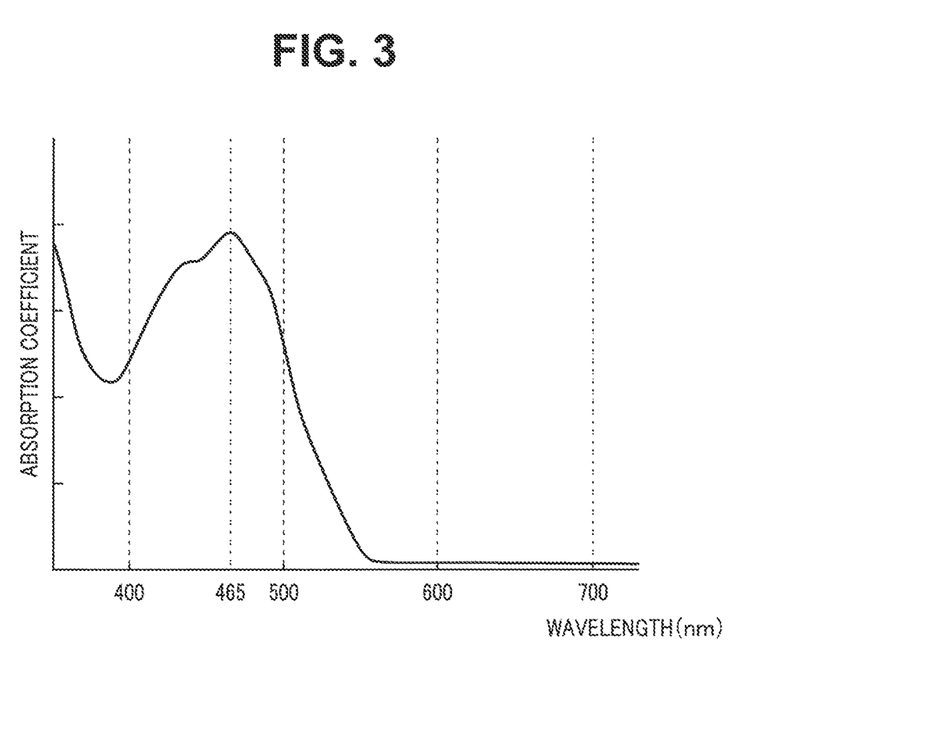
FIG. 3 is a diagram illustrating one example of an absorption characteristic of plasma.

The narrowband light source 31*d* is configured to have intensity in a blue region and generate narrowband light (hereinafter, referred to as an Nb light) having a narrower wavelength band than the Bb light. More specifically, for example, as illustrated in FIG. 2, the narrowband light source 31*d* is configured to generate light having a center wavelength set at a vicinity of 465 nm, and having a narrower wavelength band than the Bb light as the Nb light. In other words, the center wavelength of the Nb light is set as a wavelength that corresponds or substantially corresponds to a peak wavelength in an absorption characteristic of plasma as illustrated in FIG. 3. The narrowband light source 31*d* is configured to emit light or quench light in response to a light source driving signal supplied from the light source control unit 34. The narrowband light source 31*d* is configured to emit light with an emission light amount corresponding to a light source driving signal supplied from the light source control unit 34. FIG. 3 is a diagram illustrating one example of the absorption characteristic of plasma.

Note that in the present embodiment, the center wavelength of the Nb light can be set at any wavelength belonging to a range from 415 nm to 495 nm.

The multiplexer 32 is configured to be able to combine the light emitted from the light emitting unit 31 to cause the combined light to be incident on the condensing lens 33.

The condensing lens 33 is configured to collect light that goes through the multiplexer 32 and is incident, and emit the light to an incident end portion of the light guide 7.

The light source control unit 34 is, for example, configured by including a control circuit, a drive circuit and the like. The light source control unit 34 is configured to generate and output a light source driving signal for driving the respective light sources of the light emitting unit 31 in response to a control signal outputted from the processor 4.

The processor 4 is configured by having an image processing unit 41, a display control unit 42, an input I/F (interface) 43, and a control unit 44.

The image processing unit 41 is, for example, configured by including an image processing circuit or the like. Further, the image processing unit 41 is configured to apply image processing such as white balance adjustment and gamma correction to an endoscope image outputted from the endoscope 2, and output the endoscope image to which the image processing is applied to the display control unit 42 and the control unit 44.

The display control unit 42 is, for example, configured by including a display control circuit or the like. The display control unit 42 is configured to perform an operation to output a display image corresponding to a control signal outputted from the control unit 44 to the display apparatus 5. Further, the display control unit 42 is configured by having an arithmetic operation unit 42*a* and a display image generation unit 42*b*. The display control unit 42 is configured to output a processing result obtained by processing of the arithmetic operation unit 42*a* to the control unit 44 in response to a control signal outputted from the control unit 44.

The arithmetic operation unit 42*a* is configured to perform arithmetic operation processing using the endoscope image that goes through the image processing unit 41 and is outputted. Note that a specific example of the processing performed by the arithmetic operation unit 42*a* will be described later.

The display image generation unit 42*b* is configured to perform processing to generate a diagnosis assist image having visual information that allows for identifying an abnormal site included in an endoscope image by processing at least one of a color and a pattern of the endoscope image that goes through the image processing unit 41 and is outputted based on the processing result obtained by the arithmetic operation processing of the arithmetic operation unit 42a. Note that a specific example of the processing performed by the display image generation unit 42b will be described later.

The input I/F 43 is provided with one or more switches capable of making an instruction corresponding to an input operation of the user to the control unit 44. More specifically, the input I/F 43 is provided with, for example, an observation mode changeover switch (not illustrated) capable of making an instruction to set (switch) the observation mode of the endoscope system 1 to either one of the normal observation mode or the diagnosis assist mode in response to the operation of the user. Further, the input I/F 43 is provided with, for example, a release switch (not illustrated) capable of making a release instruction to cause the endoscope image obtained by picking up an image of an object by the endoscope 2 to be recorded as a still image in response to an operation of the user.

In other words, the input I/F 43 includes a function as a switching instruction unit, and is configured to be able to make an instruction to set the observation mode (of the endoscope system 1) at the time of observing the object the image of which is picked up by the endoscope 2 at either one of the normal observation mode and the diagnosis assist mode. The normal observation mode is to cause the display apparatus 5 to display the endoscope image WDI, and the diagnosis assist mode is to cause the display apparatus 5 to display the diagnosis assist image SDS obtained by processing at least one of the color and the pattern of the endoscope image SDI.

Note that according to the present embodiment, release switches having similar functions to the functions of the release switches provided at the scope switch 23 and the input I/F 43 may be provided at other apparatuses than the scope switch 23 and the input I/F 43.

More specifically, according to the present embodiment, the release switches having the similar functions to the functions of the release switches provided at the scope switch 23 and the input I/F 43 may be provided at any of a keyboard, a foot switch, a remote controller, a tablet terminal, and a filing apparatus, for example.

The control unit 44 is configured by including a control circuit, for example. The control unit 44 is configured to perform an operation corresponding to an instruction that is made in the scope switch 23 or the input I/F 43. The control unit 44 is configured to generate and output a control signal to control the operation of the image pickup device 21b. The control unit 44 is configured to generate and output control signals to control operations of the respective light sources of the light emitting unit 31 via the light source control unit 34. Further, the control unit 44 is configured by having an image recording unit 44a, and an observation state detection unit 44b.

The image recording unit 44a is configured to perform an operation to record the endoscope image that goes through the image processing unit 41 and is outputted as an observation state detecting image. The image recording unit 44a is configured to perform an operation to record the endoscope image that goes through the image processing unit 41 and is outputted as a release image (still image) when a release instruction is made. The image recording unit 44a is configured to perform an operation to record the endoscope image that goes through the image processing unit 41 and is outputted as a recorded image (still image) immediately after the observation mode of the endoscope system 1 is set at the diagnosis assist mode.

The observation state detection unit 44b is configured to perform observation state detection processing to calculate a feature value corresponding to an observation state at a time of observing an object by the endoscope 2 base on the observation state detecting image recorded in the image recording unit 44a. Note that a specific example of the processing performed by the observation state detection unit 44b will be described later.

Note that in the present embodiment, the respective units of the processor 4 may be configured as individual electronic circuits, or may be configured as circuit blocks in an integrated circuit such as FPGA (field programmable gate array). In the present embodiment, for example, the processor 4 may be configured by including one or more CPUs. Further, by properly modifying the configuration according to the present embodiment, for example, a computer not illustrated may read a program for causing the functions of the respective units of the processor 4 to be executed from a storage medium such as a memory, and may perform operations corresponding to the read program.

The display apparatus 5 includes, for example, an LCD (liquid crystal display), and is configured to be able to display a display image and the like outputted from the processor 4.

Figure 4:
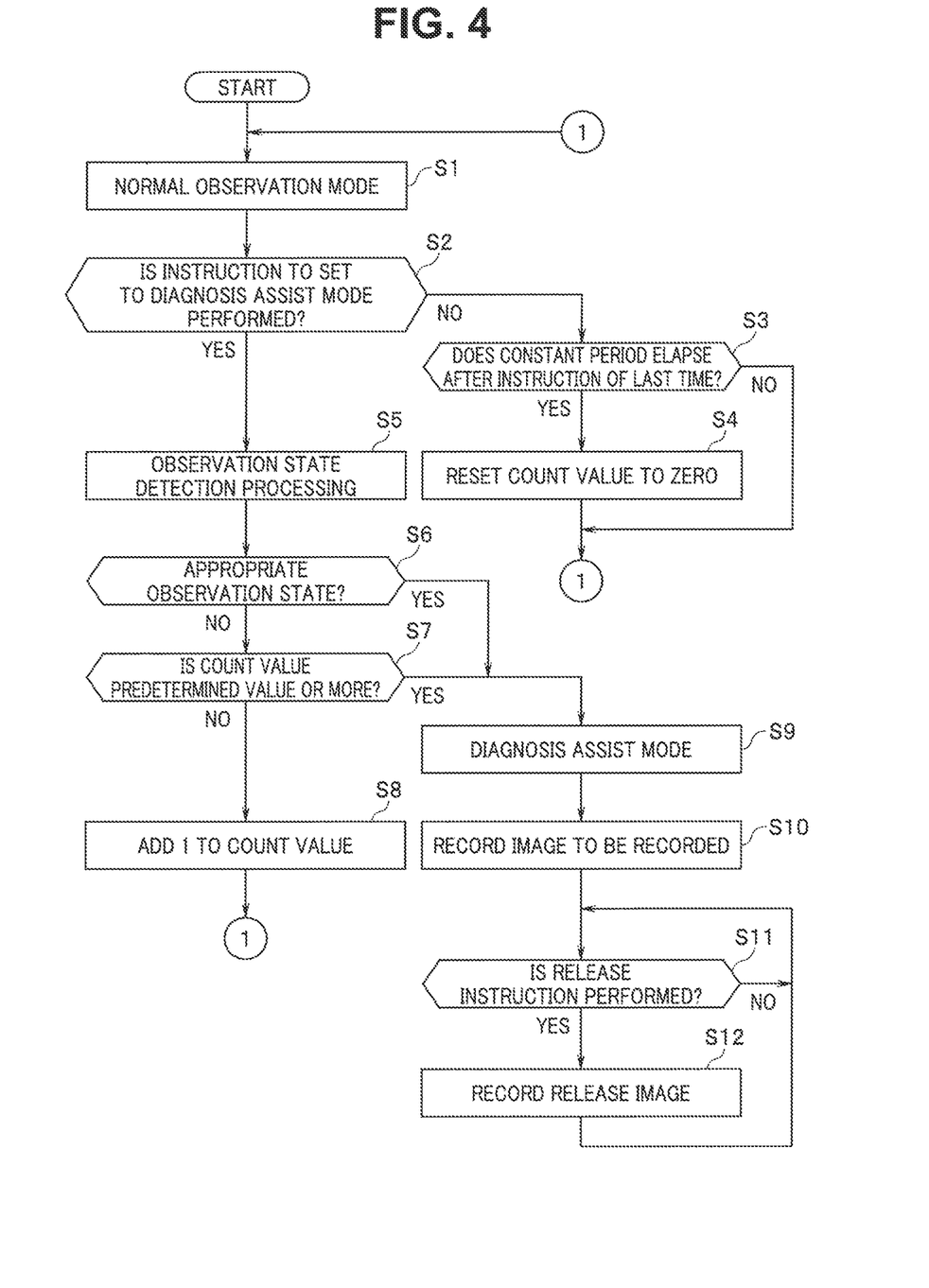
FIG. 4 is a flowchart illustrating a specific example of processing and the like that are performed in the endoscope system according to the embodiment.

Subsequently, an operation of the present embodiment will be described with reference to FIG. 4 and the like. Note that hereinafter, explanation will be made by citing an example of a case where the insertion portion 2a is inserted into a nasal cavity of an examinee, and an image of an object including living tissue (mucous membrane and the like) existing in the nasal cavity of the examinee is picked up by the image pickup unit 21. FIG. 4 is a flowchart illustrating a specific example of processing and the like that are performed in the endoscope system according to the embodiment.

A user such as a surgeon connects the respective units of the endoscope system 1 and turns on a power supply, and thereafter, makes the instruction to set the observation mode of the endoscope system 1 at the normal observation mode by operating the observation mode changeover switch of the scope switch 23 or the input I/F 43, for example.

When the control unit 44 detects that the instruction to set the observation mode of the endoscope system 1 at the normal observation mode is made, the control unit 44 generates and outputs the control signal to cause the operation corresponding to the normal observation mode to be performed (step S1 in FIG. 4). Further, the control unit 44 performs an operation to maintain the observation mode of the endoscope system 1 at the normal observation mode in response to a processing result and the like obtained by processing described later (step S1 in FIG. 4).

In step S1 in FIG. 4, the control unit 44 generates a control signal to cause the light source apparatus 3 to emit the Bb light, the Bg light, and the Br light, and outputs the control signal to the light source control unit 34. In step S1 in FIG. 4, the control unit 44 generates a control signal to cause the display apparatus 5 to display the endoscope image WDI that goes through the image processing unit 41 and is outputted, and outputs the control signal to the display control unit 42. Further, in step S1 in FIG. 4, the control unit 44 causes the image recording unit 44a to record the endoscope image WDI corresponding to a predetermined period PA that goes through the image processing unit 41 and is outputted as an observation state detecting image VDI. Note that the predetermined period PA can be set as a period corresponding to a size of the nasal cavity of the examinee, for example.

The light source control unit 34 generates and outputs a light source driving signal to cause the blue light source 31a, the green light source 31b, and the red light source 31c to emit light at a same time while causing the narrowband light source 31d to quench light in the normal observation mode, in response to a control signal outputted from the control unit 44. Subsequently, in response to the operation of the light source control unit 34 like this, in the normal observation mode, illumination light WL including the Bb light, the Bg light, and the Br light is emitted from the light source apparatus 3 (light emitting unit 31), the object is irradiated with the illumination light WL, and the endoscope image WDI obtained by picking up an image of return light (reflected light) of the illumination light WL is outputted from the image pickup unit 21 to the image processing unit 41.

The image processing unit 41 applies image processing such as white balance adjustment and gamma correction to the endoscope image WDI outputted from the endoscope 2, and outputs the endoscope image WDI to which the image processing is applied to the display control unit 42, in response to a control signal outputted from the control unit 44.

The display control unit 42 performs an operation to output the endoscope image WDI that goes through the image processing unit 41 and is outputted to the display apparatus 5 as the display image in the normal observation mode in response to the control signal outputted from the control unit 44.

The image recording unit 44a performs an operation to sequentially record the endoscope image WDI corresponding to the predetermined period PA that goes through the image processing unit 41 and is outputted as the observation state detecting image VDI in the normal observation mode. Note that the respective observation state detecting images VDI recorded in the image recording unit 44a are assumed to be given time point information that allows for identifying time points at which the observation state detecting images VDI are recorded by the image recording unit 44a, such as time stamps.

The user inserts the insertion portion 2a of the endoscope 2 into a nasal cavity of an examinee while confirming the endoscope image WDI displayed on the display apparatus 5, and disposes the distal end portion 2c in a vicinity of a desired object existing in the nasal cavity of the examinee Thereafter, the user makes an instruction to set the observation mode of the endoscope system 1 at the diagnosis assist mode by operating the observation mode changeover switch of the scope switch 23 or the input I/F 43, in a state where the distal end portion 2c of the endoscope 2 is disposed in the vicinity of the desired object.

The control unit 44 performs determination processing concerning whether or not the instruction to set the observation mode of the endoscope system 1 at the diagnosis assist mode is made (step S2 in FIG. 4).

When the control unit 44 cannot detect the instruction to set the observation mode of the endoscope system 1 at the diagnosis assist mode (S2: NO), the control unit 44 performs determination processing concerning whether or not a constant period elapses after timing when the control unit 44 detects the instruction last time (step S3 in FIG. 4).

When the control unit 44 detects that the constant period does not elapse after the timing when the control unit 44 detects the instruction to set the observation mode of the endoscope system 1 at the diagnosis assist mode last time (S3: NO), the control unit 44 performs the operation in step S1 in FIG. 4 in a state where the control unit 44 maintains a count value CNT described later.

When the control unit 44 detects that the constant period elapses after the timing when the control unit 44 detects the instruction to set the observation mode of the endoscope system 1 at the diagnosis assist mode last time (S3: YES), the control unit 44 resets the count value CNT to zero (step S4 in FIG. 4), and thereafter performs the operation in step S1 in FIG. 4.

When the control unit 44 can detect the instruction to set the observation mode of the endoscope system 1 at the diagnosis assist mode (S2: YES), the control unit 44 causes the image recording unit 44a to record the endoscope image WDI corresponding to the predetermined period PB that goes through the image processing unit 41 and is outputted as the observation state detecting image VDI. Note that the predetermined period PB can be set as the period corresponding to a size of the nasal cavity of the examinee, for example.

The image recording unit 44a performs an operation to sequentially record the endoscope images WDI outputted from the image processing unit 41 as the observation state detecting images VDI, in the predetermined period PB starting from the timing when the instruction to set the observation mode of the endoscope system 1 at the diagnosis assist mode is detected (by the control unit 44).

In other words, according to the present embodiment, the endoscope images WDI outputted from the image processing unit 41 are sequentially recorded in the image recording unit 44a as the observation state detecting images VDI in each of a predetermined period PA before the instruction to set the observation mode of the endoscope system 1 at the diagnosis assist mode is made, and the predetermined period PB corresponding to a period continuing from the predetermined period PA after the instruction is made.

The observation state detection unit 44b performs observation state detection processing to calculate a feature value FVA corresponding to an observation state immediately before the observation mode of the endoscope system 1 is switched from the normal observation mode to the diagnosis assist mode based on the observation state detecting image VDI recorded in the image recording unit 44a (step S5 in FIG. 4).

Here, a specific example of the processing that is performed by the observation state detection unit 44b will be described below.

The observation state detection unit 44b sets a plurality of calculation regions CRA by dividing the observation state detecting image VDI recorded in the image recording unit 44a.

Based on pixel values of respective pixels included in a calculation region CRA, the observation state detection unit 44b calculates the feature value FVA in the calculation region CRA.

According to the present embodiment, the feature values FVA in the respective calculation regions CRA may be calculated by using any of calculation methods cited below. Note that hereinafter, for convenience of explanation, the calculation methods will be described by setting a calculation region to be a calculation target of the feature value FVA as CRAX, a pixel value of blue in one pixel included in the calculation region CRAX as Vbm, a pixel value of green in the one pixel as Vgm, and a pixel value of red in the one pixel as Vrm.

The observation state detection unit 44b performs arithmetic operation of (Vrm+Vgm)/Vbm (arithmetic operation for standardizing a sum of the pixel value Vrm and the pixel value Vgm by the pixel value Vbm) in the respective pixels included in the calculation region CRAX, and calculates an average value of respective values obtained by the arithmetic operation as the feature value FVA, for example.

The observation state detection unit 44b performs arithmetic operation of Vrm/Vgm (arithmetic operation for standardizing the pixel value Vrm by the pixel value Vgm) in the respective pixels included in the calculation region CRAX, and calculates an average value of respective values obtained by the arithmetic operation as the feature value FVA, for example.

The observation state detection unit 44b performs arithmetic operation of Vrm/Vbm (arithmetic operation for standardizing the pixel value Vrm by the pixel value Vbm) in the respective pixels included in the calculation region CRAX, and calculates an average value of respective values obtained by the arithmetic operation as the feature value FVA, for example.

The observation state detection unit 44b performs arithmetic operation of Vgm/Vbm (arithmetic operation for standardizing the pixel value Vgm by the pixel value Vbm) in the respective pixels included in the calculation region CRAX, and calculates an average value of respective values obtained by the arithmetic operation as the feature value FVA, for example.

Note that the observation state detection unit 44b may perform arithmetic operation using a formula that reverses a denominator and a numerator of any of formulas that are (Vrm+Vgm)/Vbm, Vrm/Vgm, Vrm/Vbm, and Vgm/Vbm, and may calculate an average value of respective values obtained by the arithmetic operation as the feature value FVA.

In other words, the observation state detection unit 44b detects an observation state at a time of observing the object in the subject (in the nasal cavity) by the endoscope 2 provided with the image pickup unit 21 based on the endoscope image WDI recorded in the image recording unit 44a. The observation state detection unit 44b performs processing of setting the plurality of calculation regions CRA by dividing the endoscope image WDI, and calculating a plurality of feature values FVA corresponding to pixel values in the plurality of respective calculation regions CRA as processing to detect the observation state at a time of observing the object in the subject (in the nasal cavity) by the endoscope 2. Further, the observation state detection unit 44b acquires the feature value FVA calculated for each of the calculation regions CRA obtained by dividing the observation state detecting image VDI (endoscope image WDI) as a detection result of the observation state at the time of observing the object in the subject (in the nasal cavity) by the endoscope 2 provided with the image pickup unit 21.

The control unit 44 performs determination processing concerning whether or not the observation state at the time of observing the object in the nasal cavity by the endoscope 2 is in an appropriate observation state based on the feature values FVA calculated by the observation state detection unit 44b (step S6 in FIG. 4).

Here, a specific example of the determination processing performed by the control unit 44 in step S6 in FIG. 4 will be described below.

The control unit 44 obtains a determination result that the observation state at the time of observing the object in the nasal cavity by the endoscope 2 is an appropriate observation state when the control unit 44 detects that the feature values FVA are equal to or more than a threshold THA in all the calculation regions CRA of the observation state detecting image VDI, based on the detection result by the observation state detection unit 44b, for example. Further, the control unit 44 obtains a detection result that the observation state at the time of observing the object in the nasal cavity by the endoscope 2 is not an appropriate observation state when the control unit 44 detects that there are one or more calculation regions CRA having the feature values FVA less than the threshold value THA in the observation state detecting image VDI based on the detection result by the observation state detection unit 44b, for example. In other words, according to the processing of the control unit 44 like this, it is detected that the observation state at the time of observing the object in the subject (in the nasal cavity) by the endoscope 2 is not an appropriate observation state when one or more feature values FVA less than the threshold THA is or are included in the plurality of feature values FVA calculated in the plurality of calculation regions CRA.

The control unit 44 obtains the determination result that the observation state at the time of observing the object in the nasal cavity by the endoscope 2 is an appropriate observation state when the control unit 44 detects that a ratio of the calculation regions CRA having the feature values FVA less than a threshold THB in the observation state detecting image VDI is less than a predetermined ratio RM based on the detection result by the observation state detection unit 44b, for example. Further, the control unit 44 obtains the determination result that the observation state at the time of observing the object in the nasal cavity by the endoscope 2 is not an appropriate observation state when the control unit 44 detects that the ratio of the calculation regions CRA having the feature values FVA less than the threshold THB in the observation state detecting image VDI is equal to or more than the predetermined ratio RM based on the detection result by the observation state detection unit 44b, for example. In other words, according to the processing of the control unit 44 like this, it is detected that the observation state at the time of observing the object in the subject (in the nasal cavity) by the endoscope 2 is not an appropriate observation state, when the feature values FVA less than the threshold THA are included in a predetermined ratio or more among the plurality of feature values FVA calculated in the plurality of calculation regions CRA.

The control unit 44 calculates a difference value DVA between a feature value FVAY corresponding to one calculation region CRAY selected from the respective calculation regions CRA, and a feature value FVAZ corresponding to a calculation region CRAZ selected from the respective calculation regions CRA and different from the one calculation region CRAY, in the respective calculation regions CRA of the observation state detecting image VDI, based on the detection result by the observation state detection unit 44b, for example. The control unit 44 acquires a classification result relating to which group an absolute value |DVA| of the difference value DVA is classified into among a plurality of preset groups of pixel values according to a number of gradations of the observation state detecting image VDI, for example. The control unit 44 obtains the determination result that the observation state at the time of observing the object in the nasal cavity by the endoscope 2 is an appropriate observation state, when the control unit 44 detects that a ratio of one or more calculation regions CRGA having the absolute value |DVA| classified into the group of a low pixel value among the plurality of groups of pixel values to the observation state detecting image VDI is less than a ratio of one or more calculation regions CRGB having the absolute value |DVA| classified into a group of a high pixel value among the plurality of groups of pixel values to the observation state detecting image VDI. Further, the control unit 44 obtains the determination result that the observation state at the time of observing the object in the nasal cavity by the endoscope 2 is not an appropriate observation state, when the control unit 44 detects that the ratio of the one or more calculation regions CRGA to the observation state detecting image VDI is equal to or more than the ratio of the one or more calculation regions CRGB to the observation state detecting image VDI. In other words, according to the processing of the control unit 44 like this, a plurality of arithmetic operation values (absolute values |DVA|) indicating magnitudes of differences of the plurality of feature values FAV among the plurality of calculation regions CRA are calculated, and when arithmetic operation values that are less than a predetermined threshold are included in a predetermined ratio or more among the plurality of arithmetic operation values, it is detected that the observation state at the time of observing the object in the subject (in the nasal cavity) by the endoscope 2 is not an appropriate observation state.

According to the processing described above, the control unit 44 obtains the determination result that the observation state at the time of observing the object in the nasal cavity by the endoscope 2 is an appropriate observation state, when the control unit 44 performs the determination processing in step S6 in FIG. 4 to the observation state detecting image VDI that includes more bright regions than dark regions, for example. Further, according to the processing as described above, the control unit 44 obtains the determination result that the observation state at the time of observing the object in the nasal cavity by the endoscope 2 is an appropriate observation state, when the control unit 44 performs the determination processing in step S6 in FIG. 4 to the observation state detecting image VDI with small difference in light and dark in the image, for example.

According to the processing as described above, the control unit 44 obtains the determination result that the observation state at the time of observing the object in the nasal cavity by the endoscope 2 is not an appropriate observation state, when the control unit 44 performs the determination processing in step S6 in FIG. 4 to the observation state detecting image VDI that includes more dark regions than bright regions, for example. Further, according to the processing as described above, the control unit 44 obtains the determination result that the observation state at the time of observing the object in the nasal cavity by the endoscope 2 is not an appropriate observation state, when the control unit 44 performs the determination processing in step S6 in FIG. 4 to the observation state detecting image VDI with large difference in light and dark in the image, for example.

The control unit 44 performs an operation in step S9 in FIG. 4 described later, when the control unit 44 obtains the determination result that the observation state at the time of observing the object in the nasal cavity by the endoscope 2 is an appropriate observation state (S6: YES).

When the control unit 44 obtains the determination result that the observation state at the time of observing the object in the nasal cavity by the endoscope 2 is not an appropriate observation state (S6: NO), the control unit 44 performs determination processing concerning whether or not the count value CNT held at present is a predetermined value or more (step S7 in FIG. 4).

When the control unit 44 detects that the count value CNT held at present is the predetermined value or more (S7: YES), the control unit 44 performs an operation in step S9 in FIG. 4 described later.

When the control unit 44 detects that the count value CNT held at present is less than the predetermined value (S7: NO), the control unit 44 adds 1 to the count value CNT (step S8 in FIG. 4), and thereafter performs the operation in step S1 in FIG. 4. In other words, the count value CNT indicates a number of times the instruction to set the observation mode of the endoscope system 1 at the diagnosis assist mode is invalidated by the control unit 44 within a constant period.

According to the operations and the like described above, the control unit 44 invalidates the instruction to set the observation mode at the diagnosis assist mode that is made in the scope switch 23 or the input I/F 43, when the control unit 44 detects that the observation state at the time of observing the object in the subject (in the nasal cavity) by the endoscope 2 is not an appropriate observation state, immediately before the observation mode of the endoscope system 1 is switched from the normal observation mode to the diagnosis assist mode, based on the detection result of the observation state detection unit 44b.

The control unit 44 performs an operation in step S10 in FIG. 4 described later, after the control unit 44 generates and outputs a control signal to cause the operation corresponding to the diagnosis assist mode to be performed (step S9 in FIG. 4). In other words, the control unit 44 performs control to set the observation mode at the diagnosis assist mode, when the control unit 44 detects that the observation state at the time of observing the object in the subject (in the nasal cavity) by the endoscope 2 is an appropriate observation state (when a flow shifts from step S6 to step S9 in FIG. 4), immediately before the observation mode of the endoscope system 1 is switched from the normal observation mode to the diagnosis assist mode. The control unit 44 performs control to set the observation mode at the diagnosis assist mode, when the number of times the control unit 44 invalidates the instruction to set the observation mode of the endoscope system 1 at the diagnosis assist mode in the constant period is equal to or more than a predetermined number (when the flow shifts from step S7 to step S9 in FIG. 4).

The control unit 44 generates a control signal to cause the Nb light, the Bg light, and the Br light to be emitted from the light source apparatus 3, and outputs the control signal to the light source control unit 34 in step S9 in FIG. 4. Further, the control unit 44 generates a control signal to cause the display apparatus 5 to display the diagnosis assist image SDS corresponding to the endoscope image SDI that goes through the image processing unit 41 and is outputted, and outputs the control signal to the display control unit 42, in step S9 in FIG. 4.

The light source control unit 34 generates and outputs a light source driving signal to cause the green light source 31b, the red light source 31c, and the narrowband light source 31d to emit light at the same time while causing the blue light source 31a to quench light in the diagnosis assist mode, in response to the control signal outputted from the control unit 44. Subsequently, in response to the operation of the light source control unit 34 like this, in the diagnosis assist mode, illumination light SL including the Nb light, the Bg light, and the Br light is emitted from the light source apparatus 3 (light emitting unit 31), the object is irradiated with the illumination light SL, and the endoscope image SDI obtained by picking up an image of return light (reflected light) of the illumination light SL is outputted to the image processing unit 41 from the image pickup unit 21.

The image processing unit 41 applies image processing such as white balance adjustment and gamma correction to the endoscope image SDI outputted from the endoscope 2, and outputs the endoscope image SDI to which the image processing is applied to the display control unit 42 and the control unit 44 respectively.

The display control unit 42 performs an operation to generate a diagnosis assist image SDS corresponding to the endoscope image SDI that goes through the image processing unit 41 and is outputted, and output the generated diagnosis assist image SDS to the display apparatus 5 as the display image, in the diagnosis assist mode, in response to the control signal outputted from the control unit 44.

Here, a specific example of a generation method of the diagnosis assist image SDS displayed on the display apparatus 5 at a time of the diagnosis assist mode will be described.

The arithmetic operation unit 42a performs arithmetic operation processing to calculate an index value IV indicating a degree of abnormality in living tissue included in the endoscope image SDI, in respective pixels of the endoscope image SDI that goes through the image processing unit 41 and is outputted. More specifically, the arithmetic operation unit 42a calculates the index value IV by using a same calculation method as any one of the calculation methods of the feature value FVA described above, for example. Subsequently, the arithmetic operation unit 42a acquires a calculation result of the index values IV in the respective pixels of the endoscope image SDI as a processing result of the arithmetic operation processing.

The display image generation unit 42b generates the diagnosis assist image SDS having visual information that allows for identifying an abnormal site included in the endoscope image by processing at least one of a color and a pattern of the endoscope image SDI that goes through the image processing unit 41 and is outputted, based on the processing result obtained by the arithmetic operation processing of the arithmetic operation unit 42a.

More specifically, the display image generation unit 42b generates the diagnosis assist image SDS by performing processing of classifying the index values IV calculated in the respective pixels of the endoscope image SDI into any of a plurality of numeric value ranges based on the processing result obtained by the arithmetic operation processing of the arithmetic operation unit 42a, and replacing pixel information included in the respective pixels with pixel information corresponding to colors and/or patterns corresponding to the numeric value ranges after classification. According to the processing like this, the diagnosis assist image SDS in which different colors and/or patterns are added to a normal site included in the endoscope image SDI and an abnormal site included in the endoscope image SDI is generated.

According to the present embodiment, for example, when the control unit 44 performs the operation in step S1 after going through step S7 and step S8 in FIG. 4, the control unit 44 may perform an operation of generating a control signal to cause the display apparatus 5 to display visual information ARA with the endoscope image WDI and outputting the control signal to the display control unit 42. The visual information ARA is an alert message or the like capable of informing that shift to the diagnosis assist mode is stopped because the observation state at the time of observing the object in the subject (in the nasal cavity) by the endoscope 2 is not an appropriate observation state. Further, according to the present embodiment, a voice corresponding to the aforementioned visual information ARA may be generated from a speaker or the like not illustrated, for example.

According to the present embodiment, for example, when the control unit 44 performs the operation in step S9 after goring through step S7 in FIG. 4, the control unit 44 may perform an operation of generating a control signal to cause the display apparatus 5 to display visual information ARB with the diagnosis assist image SDS and outputting the control signal to the display control unit 42. The visual information ARB is an alert message or the like capable of informing that the observation mode shifts to the diagnosis assist mode although the observation state at the time of observing the object in the subject (in the nasal cavity) by the endoscope 2 is not an appropriate observation state. Further, according to the present embodiment, a voice corresponding to the aforementioned visual information ARB may be generated from a speaker or the like not illustrated, for example.

According to the present embodiment, for example, when the control unit 44 obtains the determination result that the observation state at the time of observing the object in the nasal cavity by the endoscope 2 is not an appropriate observation state by the determination processing in step S6 in FIG. 4, the control unit 44 may skip step S7 in FIG. 4 and perform the processing in step S8 and the operation in step S1. In the case like this, the observation mode of the endoscope system 1 is maintained at the normal observation mode until the determination result that the observation state at the time of observing the object in the nasal cavity by the endoscope 2 is an appropriate observation state is obtained by the determination processing in step S6 in FIG. 4, regardless of the magnitude of the count value CNT added by the processing in step S8 in FIG. 4.

Figure 5:
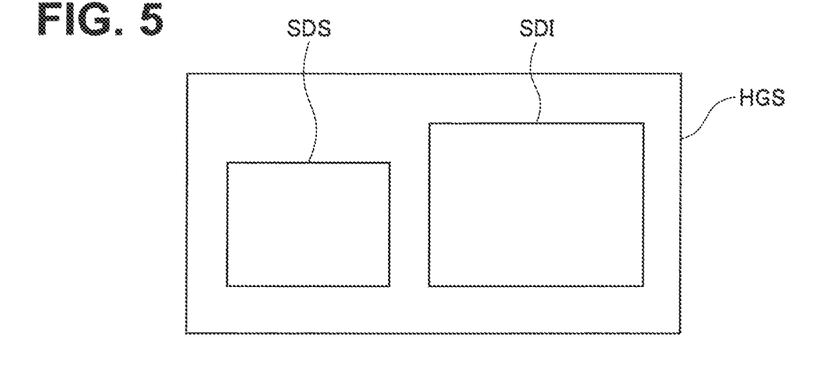
FIG. 5 is a view illustrating one example of an image that is displayed in response to an operation and the like of the endoscope system according to the embodiment.

According to the present embodiment, the actions performed by the control unit 44 is not limited to generating the control signal to cause the display apparatus 5 to display the diagnosis assist image SDS alone and outputting the control signal to the display control unit 42, and the control unit 44 may generate a control signal to cause the display apparatus 5 to display the endoscope image SDI and the diagnosis assist image SDS in combination and output the control signal to the display control unit 42, for example, when setting the observation mode of the endoscope system 1 at the diagnosis assist mode. According to the operation of the control unit 44 like this, an operation to output a display image HGS including the two images that are the endoscope image SDI and the diagnosis assist image SDS to the display apparatus 5 as illustrated in FIG. 5, for example, is performed in the display control unit 42. Note that the display image HGS may include a character string indicating a predetermined statistic such as an average value of the index values IV, for example. FIG. 5 is a view illustrating one example of the image that is displayed in response to the operation and the like of the endoscope system according to the embodiment.

The control unit 44 causes the image recording unit 44a to record the endoscope image SDI that goes through the image processing unit 41 and is outputted as a recorded image SDM immediately after shifting the observation mode of the endoscope system 1 to the diagnosis assist mode (step S10 in FIG. 4), and performs an operation in step S11 in FIG. 4 described later after causing the image recording unit 44a to record index values IVM of the respective pixels calculated by the arithmetic operation unit 42a when generating the diagnosis assist image SDS corresponding to the endoscope image SDI by associating the index values IVM with the recorded image SDM.

Note that according to the present embodiment, the action performed by the control unit 44 is not limited to causing the image recording unit 44a to record the index values IVM of the respective pixels calculated by the arithmetic operation unit 42a by associating the index values IVM with the recorded image SDM, and the control unit 44 may cause the image recording unit 44a to record arithmetic operation values CVM calculated by using the index values IVM of the respective pixels by associating the arithmetic operation values CVM with the recorded image SDM, in step S10 in FIG. 4.

More specifically, according to the present embodiment, the control unit 44 may cause the image recording unit 44a to record difference values DVB between the index values IVM of the respective pixels calculated by the arithmetic operation unit 42a and a threshold THC as the arithmetic operation values CVM by associating the difference values DVB with the recorded image SDM, for example. According to the present embodiment, the control unit 44 may cause the image recording unit 44a to record an average value AVA of the index values IVM of the respective pixels calculated by the arithmetic operation unit 42a as the arithmetic operation value CVM by associating the average value AVA with the recorded image SDM, for example. Further, according to the present embodiment, the control unit 44 may cause the image recording unit 44a to record an average value AVB of the difference values DVB as the arithmetic operation value CVM by associating the average value AVB with the recorded image SDM, for example.

According to the present embodiment, the action performed by the control unit 44 is not limited to causing the image recording unit 44a to record information in which the index values IVM or the arithmetic operation values CVM are associated with the recorded image SDM, and the control unit 44 may cause an apparatus other than the processor 4 to record the information.

More specifically, the control unit 44 may cause, for example, any one of the scope memory provided in the endoscope 2, the display apparatus 5, the tablet terminal, and the filing apparatus to record the information in which the index values IVM or the arithmetic operation values CVM are associated with the recorded image SDM.

The control unit 44 performs determination processing concerning whether or not a release instruction is made (step S11 in FIG. 4).

When the control unit 44 cannot detect the release instruction (S11: NO), the control unit 44 shifts to a standby state while maintaining the observation mode of the endoscope system 1 at the diagnosis assist mode.

When the control unit 44 can detect the release instruction (S11: YES), the control unit 44 causes the image recording unit 44a to record the endoscope image SDI that goes through the image processing unit 41 and is outputted immediately after the release instruction as a release image SDR (step S12 in FIG. 4), and causes the image recording unit 44a to record index values IVR of the respective pixels calculated by the arithmetic operation unit 42a when generating the diagnosis assist image SDS corresponding to the endoscope image SDI by associating the index values IVR with the release image SDR. Thereafter, the control unit 44 shifts to the standby state while maintaining the observation mode of the endoscope system 1 at the diagnosis assist mode.

Note that according to the present embodiment, the action performed by the control unit 44 is not limited to causing the image recording unit 44a to record the index values IVR of the respective pixels calculated by the arithmetic operation unit 42a by associating the index values IVR with the release image SDR, and the control unit 44 may cause the image recording unit 44a to record arithmetic operation values CVR calculated by using the index values IVR of the respective pixels by associating the arithmetic operation values CVR with the release image SDR, in step S12 in FIG. 4.

More specifically, according to the present embodiment, the control unit 44 may cause the image recording unit 44a to record difference values DVC between the index values IVR of the respective pixels calculated by the arithmetic operation unit 42a and a threshold THD as the arithmetic operation values CVR by associating the difference values DVC with the release image SDR, for example. According to the present embodiment, the control unit 44 may cause the image recording unit 44a to record an average value AVC of the index values IVR of the respective pixels calculated by the arithmetic operation unit 42a as the arithmetic operation value CVR by associating the average value AVC with the release image SDR, for example. Further, according to the present embodiment, the control unit 44 may cause the image recording unit 44a to record the average value AVD of the difference values DVC as the arithmetic operation value CVR by associating the average value AVD with the release image SDR, for example.

As described above, according to the present embodiment, it is possible to interrupt the operation to shift the observation mode of the endoscope system 1 to the diagnosis assist mode for at least a constant period, when it is confirmed that the observation state at the time of observing the object in the nasal cavity by the endoscope 2 is not an appropriate observation state (for example, at least one of the observation direction and the brightness at the time of observing the object in the nasal cavity by the endoscope 2 is not in a state unsuitable for observation), before the observation mode of the endoscope system 1 is switched from the normal observation mode to the diagnosis assist mode. As described above, according to the present embodiment, the operation to shift the observation mode of the endoscope system 1 to the diagnosis assist mode is performed when it is confirmed that the observation state at the time of observing the object in the nasal cavity by the endoscope 2 is an appropriate observation state (for example, both the observation direction and the brightness at the time of observing the object in the nasal cavity by the endoscope 2 are in states suitable for observation) before the observation mode of the endoscope system 1 is switched from the normal observation mode to the diagnosis assist mode. As described above, according to the present embodiment, it is possible to perform the operation for informing that the observation state at the time of observing the object in the nasal cavity by the endoscope 2 is not an appropriate observation state in either a time before the observation mode of the endoscope system 1 is switched from the normal observation mode to the diagnosis assist mode, and a time after the observation mode is switched from the normal observation mode to the diagnosis assist mode. Consequently, according to the present embodiment, it is possible to prevent the diagnosis assist image SDS that may induce misdiagnosis due to deterioration of the observation state at the time of observing the object by the endoscope 2 from being displayed as much as possible. As a result, it is possible to secure precision at a time of performing diagnosis by the image in which at least one of the color and the pattern of the endoscope image is processed.

Figure 6:
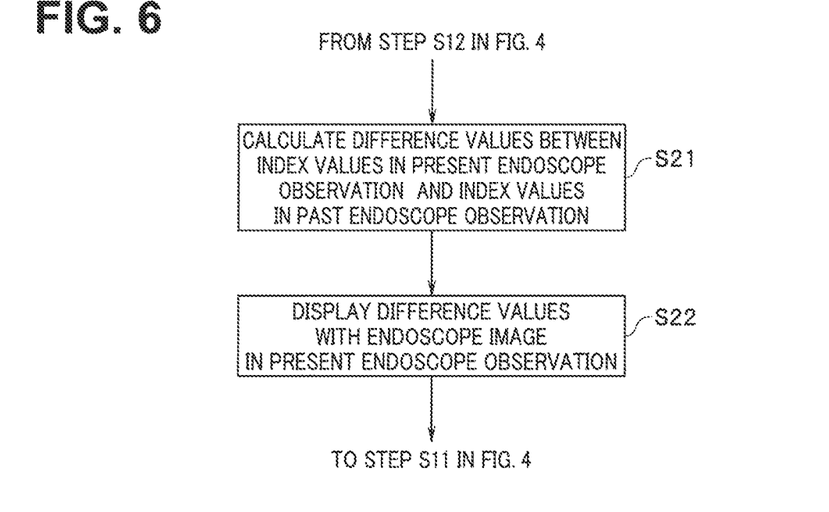
FIG. 6 is a flowchart illustrating a part of a specific example of processing and the like that are performed in the endoscope system according to the embodiment.

Note that according to the present embodiment, the control unit 44 may perform control to cause the display apparatus to display visual information indicating differences between values that are used at a time of generating the diagnosis assist image SDS in observation of an object in a subject (in a nasal cavity) performed at present, and values that are used at a time of generating the diagnosis assist image SDS in observation of the object in the subject (in the nasal cavity) performed in the past, when the control unit 44 performs control to set the observation mode of the endoscope system 1 at the diagnosis assist mode, for example. A specific example of the operation like this will be described below with reference to FIG. 6 and the like as the operation that is performed after step S12 in FIG. 4. Note that hereinafter, specific explanations concerning the parts to which the operations and the like already described are applicable will be properly omitted. Hereinafter, the case where the index values IVR are recorded in the image recording unit 44*a* in a state where the index values IVR are associated with the release image SDR will be described by being cited as an example, unless otherwise specified. FIG. 6 is a flowchart illustrating a part of a specific example of processing and the like that are performed in the endoscope system according to the embodiment.

After the control unit 44 performs the operation in step S12 in FIG. 4, the control unit 44 performs processing to calculate difference values DVRA indicating differences between index values IVRC associated with a release image SDRC recorded in the image recording unit 44*a* in present endoscope observation, and index values IVRP associated with a release image SDRP recorded in the image recording unit 44*a* in past endoscope observation (step S21 in FIG. 6).

The control unit 44 generates a control signal to cause a calculation result of the difference values DVRA obtained as a processing result of step S21 in FIG. 6 to be displayed with the endoscope image SDI acquired in the present endoscope observation, and outputs the control signal to the display control unit 42 (step S22 in FIG. 6). After the control unit 44 performs an operation of step S22 in FIG. 6, the control unit 44 shifts to a standby state while maintaining the observation mode of the endoscope system 1 at the diagnosis assist mode.

The display control unit 42 performs an operation to generate a diagnosis assist image SDT by processing at least one of a color and a pattern of the endoscope image SDI acquired in the present endoscope observation based on the difference values DVRA, and output the generated diagnosis assist image SDT to the display apparatus 5 as a display image, for example, in response to a control signal outputted from the control unit 44.

More specifically, the display control unit 42 generates an image obtained by processing the endoscope image SDI so that regions where the difference values DVRA are zero, and regions where the difference values are not zero have visually discriminable colors and/or patterns, for example, as the diagnosis assist image SDT.

Alternatively, the display control unit 42 generates an image obtained by processing the endoscope image SDI so that the endoscope image SDI has colors and/or patterns that differ according to magnitudes of the difference values DVRA, for example, as the diagnosis support image SDT.

Alternatively, the display control unit 42 generates an image obtained by processing the endoscope image SDI so that the endoscope image SDI has colors and/or patterns that differ according to the magnitudes of the differential values DVRA in the regions where the difference values DVRA are not zero, for example, as the diagnosis support image SDT.

Figure 7:
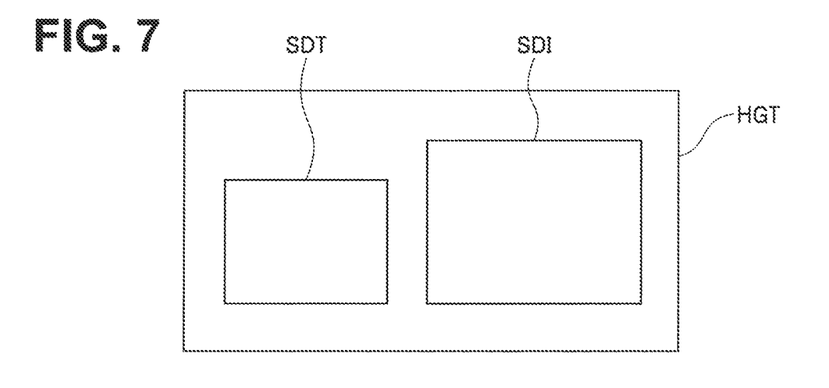
FIG. 7 is a view illustrating one example of an image that is displayed in response to an operation or the like of the endoscope system according to the embodiment.
Figure 8:
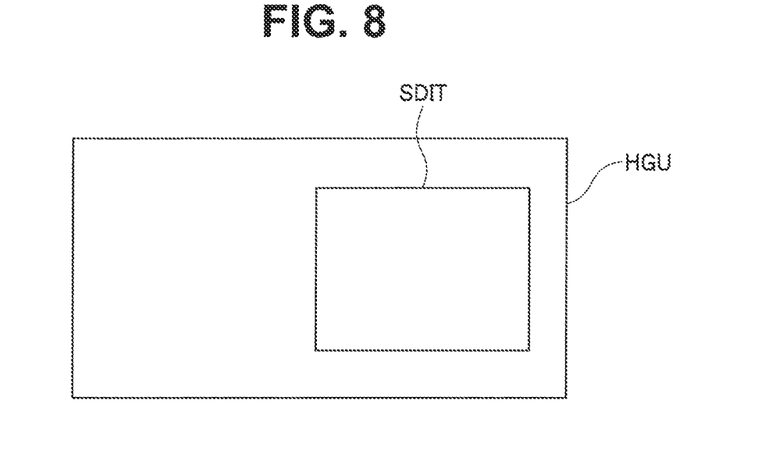
FIG. 8 is a view illustrating one example of a selection screen that is displayed in response to an operation or the like of the endoscope system according to the embodiment.

Note that the display control unit 42 may perform an operation to output a display image HGT including two images that are the endoscope image SDI acquired in the present endoscope observation, and the diagnosis assist image SDT generated based on the endoscope image SDI and the difference values DVRA to the display apparatus 5, as illustrated in FIG. 7, for example, in response to a control signal outputted from the control unit 44. The display image HGT may include a character string indicating a predetermined statistic value such as an average value of the index values IVRC, for example. Further, the display control unit 42 may perform an operation to output a display image HGU including a superimposed image SDIT in which the endoscope image SDI and the diagnosis assist image SDT are superimposed on each other to the display apparatus 5, as illustrated in FIG. 8, for example. FIG. 7 and FIG. 8 are views illustrating examples of the image displayed according to the operations and the like of the endoscope system according to the embodiment.

The diagnosis assist image SDT is not limited to being displayed on the display apparatus 5, and may be displayed on an external apparatus such as an electronic clinical chart that is connected to the processor 4, for example.

According to the present embodiment, the diagnosis assist image SDT is not limited to being generated by using the index values IVRP recorded in the image recording unit 44*a*, and may be generated by using the past index values IVRP recorded in an external apparatus such as an electronic clinical chart that is connected to the processor 4, for example. In other words, according to the present embodiment, the control unit 44 may calculate difference values DVRA indicating differences between the index values IVRC associated with the release image SDRC recorded in the image recording unit 44*a*, and the index values IVRP associated with the past release image SDRP recorded in the external apparatus that is connected to the processor 4.

According to the present embodiment, for example, the control unit 44 may perform processing to calculate difference values DVRB indicating differences between arithmetic operation values CVRC associated with the release image SDRC recorded in the image recording unit 44*a* in the present endoscope observation, and arithmetic operation values CVRP associated with the recorded image SDRP recorded in the image recording unit 44*a* in the past endoscope observation, and may generate a control signal to cause a calculation result of the difference values DVRB to be displayed with the endoscope image SDI acquired in the present endoscope observation and output the control signal to the display control unit 42.

According to the present embodiment, for example, the control unit 44 may perform processing to calculate difference values DVMA indicating differences between index values IVMC associated with a recorded image SDMC recorded in the image recording unit 44*a* in the present endoscope observation, and index values IVMP associated with a recorded image SDMP recorded in the image recording unit 44*a* in the past endoscope observation, and may generate a control signal to cause a calculation result of the difference values DVMA to be displayed with the endoscope image SDI acquired in the present endoscope observation and output the control signal to the display control unit 42.

According to the present embodiment, for example, the control unit 44 may perform processing to calculate difference values DVMB indicating differences between arithmetic operation values CVMC associated with the recorded image SDMC recorded in the image recording unit 44*a* in the present endoscope observation, and arithmetic operation values CVMP associated with the recorded image SDMP recorded in the image recording unit 44*a* in the past endoscope observation, and may generate a control signal to cause a calculation result of the difference values DVMB to be displayed with the endoscope image SDI acquired in the present endoscope observation and output the control signal to the display control unit 42.

Figure 9:
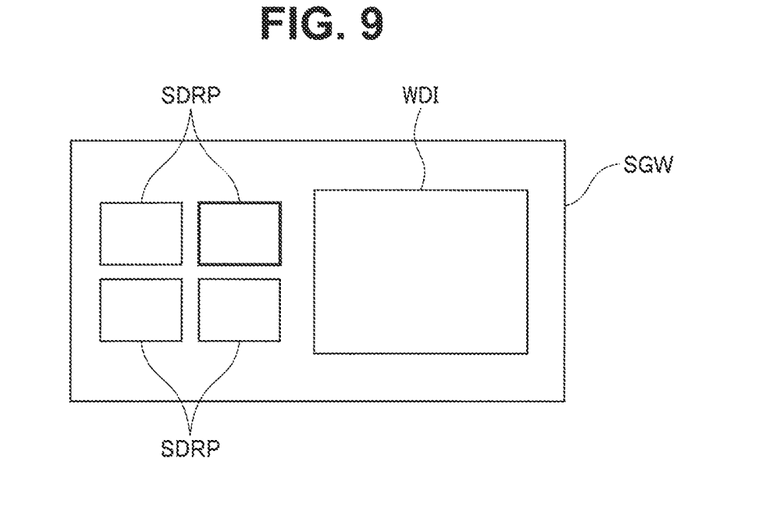
FIG. 9 is a view illustrating one example of a selection screen that is displayed in response to the operation or the like of the endoscope system according to the embodiment.

According to the present embodiment, for example, the control unit 44 may perform an operation to cause a selection screen that enables a user to select an image used for generation of the diagnosis assist image SDT from a plurality of release images SDRP to be displayed, when the control unit 44 detects that a plurality of kinds of information in which the index values IVRP are associated with the release images SDRP are recorded in the image recording unit 44a, before the control unit 44 performs an operation to set the observation mode of the endoscope system 1 at the diagnosis assist mode. According to the operation of the control unit 44 like this, for example, an operation to output a selection screen SGW as illustrated in FIG. 9 to the display apparatus 5 is performed in the display control unit 42. The selection screen SGW includes the endoscope image WDI acquired in the present endoscope observation, and thumbnails corresponding to a plurality of release images SDRP acquired in the past endoscope observation, and enables a desired image to be selected corresponding to the operation of the scope switch 23 or the input I/F 43 from the plurality of release images SDRP. FIG. 9 is a view illustrating one example of a selection screen displayed in response to the operation or the like of the endoscope system according to the embodiment.

According to the present embodiment, for example, the control unit 44 may perform an operation to cause a selection screen that enables the user to select an image used for generation of the diagnosis assist image SDT from one or more release images SDRP and the recorded images SDMP to be displayed, when the control unit 44 detects that the information with the index values IVMP associated with the recorded image SDMP, and the information with the index values IVRP associated with the release image SDRP are recorded in the image recording unit 44a, before the control unit 44 performs the operation to set the observation mode of the endoscope system 1 at the diagnosis assist mode.

According to the present embodiment, for example, a switch SWA (not illustrated) may be provided at the input I/F 43. The switch SWA is configured as a switch to instruct the control unit 44 to perform observation in a predetermined observation scene. Further, according to the present embodiment, for example, the control unit 44 may select an image used for generation of the diagnosis assist image SDT from the release images SDRP acquired in the past in the predetermined observation scene, when the control unit 44 detects that a plurality of kinds of information in which the index values IVRP and the release images SDRP are associated are recorded in the image recording unit 44a, and detects that the instruction in the switch SWA (not illustrated) is made, before the control unit 44 performs the operation to set the observation mode of the endoscope system 1 at the diagnosis assist mode. Note that the aforementioned predetermined observation scene may be set to have a combination of, for example, one of respective cavities (a frontal sinus, an ethmoidal sinus, a maxillary sinus, or a sphenoidal sinus) formed in a paranasal sinus and an observation distance (a near view or a distant view) in endoscope observation.

According to the present embodiment, for example, a switch SWB (not illustrated) may be provided at the input I/F 43. The switch SWB is configured as a switch to set communication with an external apparatus such as an electronic clinical chart that works with the endoscope system 1 to be on or off. Further, according to the present embodiment, for example, the control unit 44 may select an image used for generation of the diagnosis assist image SDT from the release images SDRP recorded in an external apparatus, when the control unit 44 detects that a plurality of kinds of information in which the index values IVRP and the release images SDRP are associated are recorded in the external apparatus, and that the switch SWB (not illustrated) is turned on respectively, before the control unit 44 performs the operation to set the observation mode of the endoscope system 1 at the diagnosis assist mode.

It goes without saying that the present invention is not limited to the aforementioned embodiment, and various modifications and applications can be made within the range without departing from the gist of the invention.

What is claimed is:

1. An endoscope system comprising:
a light source configured to generate either one of first illumination light and second illumination light as illumination light for illuminating an object;
an image pickup apparatus configured to obtain an image by picking up an image of the object illuminated by the illumination light; and
a processor,
wherein the processor is configured to
make an instruction to set an observation mode of the endoscope system at either one of a first observation mode in which a display apparatus is caused to display a first image obtained by picking up an image of the object illuminated by the first illumination light, and a second observation mode in which the display apparatus is caused to display a third image obtained by processing at least one of a color and a pattern of a second image obtained by picking up an image of the object illuminated by the second illumination light,
detect an observation state at a time of observing the object by an endoscope provided with the image pickup apparatus, based on a feature value calculated from pixel values included in pixels forming the first image, and
invalidate an instruction to set the observation mode of the endoscope system at the second observation mode, when the processor detects that the observation state at the time of observing the object by the endoscope is not an appropriate observation state based on a result of the detection, immediately before the observation mode of the endoscope system is switched from the first observation mode to the second observation mode.

2. The endoscope system according to claim 1, wherein the processor performs control to set the observation mode of the endoscope system at the second observation mode, when the processor detects that the observation state at the time of observing the object by the endoscope is an appropriate observation state based on the result of the detection, immediately before the observation mode of the endoscope system is switched from the first observation mode to the second observation mode.

3. The endoscope system according to claim 1, wherein the processor further performs control to cause visual information to be displayed with the first image, the visual information being capable of informing that shift to the second observation mode is stopped because the observation state at the time of observing the object by the endoscope is not an appropriate observation state.

4. The endoscope system according to claim 1, wherein the processor performs control to set the observation mode of the endoscope system at the second observation mode, when a number of times the processor invalidates the instruction to set the observation mode of the endoscope system at the second observation mode in a constant period is equal to or more than a predetermined number.

5. The endoscope system according to claim 4, wherein the processor further performs control to cause visual information to be displayed with the third image, the visual information being capable of informing that the observation mode shifts to the second observation mode although the observation state at the time of observing the object by the endoscope is not an appropriate observation state.

6. The endoscope system according to claim 1, wherein the processor performs processing of setting a plurality of calculation regions by dividing the first image, and calculating the feature value in plurality corresponding to the pixel values in the plurality of respective calculation regions, as processing to detect the observation state at the time of observing the object by the endoscope.

7. The endoscope system according to claim 6, wherein the processor detects that the observation state at the time of observing the object by the endoscope is not an appropriate observation state, when the feature value in plurality include one or more feature values that are less than a predetermined threshold.

8. The endoscope system according to claim 6, wherein the processor detects that the observation state at the time of observing the object by the endoscope is not an appropriate observation state, when the feature value in plurality include feature values that are less than a predetermined threshold in a predetermined ratio or more.

9. The endoscope system according to claim 6, wherein the processor calculates a plurality of arithmetic operation values indicating magnitudes of differences of the feature value in plurality among the plurality of calculation regions, and the processor detects that the observation state at the time of observing the object by the endoscope is not an appropriate observation state, when the plurality of arithmetic operation values include arithmetic operation values that are less than a predetermined threshold in a predetermined ratio or more.

10. The endoscope system according to claim 2, wherein the processor performs control to cause the second image and the third image to be displayed in combination when the processor sets the observation mode of the endoscope system at the second observation mode.

11. The endoscope system according to claim 2, wherein the processor performs control to cause the display apparatus to display visual information indicating a difference between a value that is used at a time of generating the third image in observation of the object performed at present, and a value that is used at a time of generating the third image in observation of the object performed in a past, when the processor performs control to set the observation mode of the endoscope system at the second observation mode.

12. The endoscope system according to claim 1, wherein the processor calculates the feature value from a plurality of pixel values of different colors configuring the pixels, as processing to detect the observation state at the time of observing the object by the endoscope.

13. The endoscope system according to claim 1, wherein the appropriate observation state is determined by a magnitude of the feature value.

14. An operation method of an endoscope system, comprising:
generating, by a light source, either one of first illumination light and second illumination light as illumination light for illuminating an object;
acquiring, by an image pickup apparatus, an image by picking up an image of the object illuminated by the illumination light, and
making, by a processor, an instruction to set an observation mode of the endoscope system at either one of a first observation mode in which a display apparatus is caused to display a first image obtained by picking up an image of the object illuminated by the first illumination light, and a second observation mode in which the display apparatus is caused to display a third image obtained by processing at least one of a color and a pattern of a second image obtained by picking up an image of the object illuminated by the second illumination light,
detecting, by the processor, an observation state at a time of observing the object by an endoscope provided with the image pickup apparatus based on a feature value calculated from pixel values included in pixels forming the first image, and
invalidating, by the processor, an instruction to set the observation mode of the endoscope system at the second observation mode, when detecting that the observation state at the time of observing the object by the endoscope is not an appropriate observation state based on a result of the detection, immediately before the observation mode of the endoscope system is switched from the first observation mode to the second observation mode.

15. A computer-readable non-transitory recording medium recording an operation program of an endoscope system, the recording medium causing the endoscope system to execute:
processing of generating either one of first illumination light and second illumination light as illumination light for illuminating an object;
processing of acquiring an image by picking up an image of the object illuminated by the illumination light;
processing of making an instruction to set an observation mode of the endoscope system at either one of a first observation mode in which a display apparatus is caused to display a first image obtained by picking up an image of the object illuminated by the first illumination light, and a second observation mode in which the display apparatus is caused to display a third image obtained by processing at least one of a color and a pattern of a second image obtained by picking up an image of the object illuminated by the second illumination light;
processing of detecting an observation state at a time of observing the object by an endoscope provided with an image pickup apparatus based on a feature value calculated from pixel values included in pixels forming the first image; and
processing of invalidating an instruction to set the observation mode of the endoscope system at the second observation mode, when detecting that the observation state at the time of observing the object by the endoscope is not an appropriate observation state based on a result of the detection, immediately before the observation mode of the endoscope system is switched from the first observation mode to the second observation mode.

* * * * *